US011691013B2

(12) United States Patent
Mower

(10) Patent No.: US 11,691,013 B2
(45) Date of Patent: Jul. 4, 2023

(54) BIPHASIC NEURAL STIMULATION TO IMPROVE CEREBRAL CONDUCTION SPEED AND MITOCHONDRIAL FUNCTIONING

(71) Applicant: ROCKY MOUNTAIN BIPHASIC, INC., South Minneapolis, MN (US)

(72) Inventor: Morton M. Mower, Denver, CO (US)

(73) Assignee: Rocky Mountain BiPhasic, Inc., Minneapolis, MN (US)

( * ) Notice: Subject to any disclaimer, the term of this patent is extended or adjusted under 35 U.S.C. 154(b) by 0 days.

(21) Appl. No.: 17/243,633

(22) Filed: Apr. 29, 2021

(65) Prior Publication Data
US 2022/0096836 A1 Mar. 31, 2022

Related U.S. Application Data

(60) Provisional application No. 63/084,643, filed on Sep. 29, 2020.

(51) Int. Cl.
*A61N 1/36* (2006.01)
*A61N 1/04* (2006.01)
*A61N 1/05* (2006.01)

(52) U.S. Cl.
CPC ....... *A61N 1/36082* (2013.01); *A61N 1/0456* (2013.01); *A61N 1/0529* (2013.01); *A61N 1/36053* (2013.01); *A61N 1/36064* (2013.01); *A61N 1/36175* (2013.01)

(58) Field of Classification Search
CPC .............. A61N 1/36082; A61N 1/0456; A61N 1/0529; A61N 1/36053; A61N 1/36064; A61N 1/36175
See application file for complete search history.

(56) References Cited

U.S. PATENT DOCUMENTS

| 2007/0067004 | A1 | 3/2007 | Boveja et al. | |
| 2007/0213786 | A1 | 9/2007 | Sackellares et al. | |
| 2012/0259382 | A1* | 10/2012 | Trier | A61N 1/36071 |
| | | | | 607/46 |
| 2013/0079834 | A1 | 3/2013 | Levine | |
| 2014/0142653 | A1* | 5/2014 | Osorio | A61N 1/36114 |
| | | | | 607/45 |

(Continued)

OTHER PUBLICATIONS

International Search Report and Written Opinion dated Feb. 15, 2022 in PCT/US21/50402, 18 pages.

*Primary Examiner* — Amanda K Hulbert
*Assistant Examiner* — Philip C Edwards
(74) *Attorney, Agent, or Firm* — Winthrop & Weinstine, P.A.

(57) ABSTRACT

Methods, devices and systems to improve neural stimulation by applying biphasic waveforms including a positive anodal pulse followed by a negative cathodal pulse to speed conduction and improve mitochondrial function in conditions such as cerebellar dysfunction (such as gluten ataxia, spinocerebellar ataxia, and Alzheimer's disease). Improved neural stimulation of more distal brain structures may interrupt epileptic seizures. Additionally, biphasic waveforms including a positive anodal pulse followed by a negative cathodal pulse speed wound healing by lowering the cell membrane potential of the skin, and may stimulate the release of hormonal secretions or insulin by proper placement of electrodes.

9 Claims, 14 Drawing Sheets

(56) References Cited

U.S. PATENT DOCUMENTS

| | | |
|---|---|---|
| 2014/0288620 A1* | 9/2014 | DiLorenzo ......... A61N 1/36053 607/62 |
| 2015/0018699 A1 | 1/2015 | Zeng et al. |
| 2017/0072201 A1 | 3/2017 | Morshead et al. |
| 2019/0046800 A1 | 2/2019 | Doan et al. |
| 2020/0261730 A1 | 8/2020 | Mower |

\* cited by examiner

BIPHASIC NEURAL STIMULATION TO IMPROVE CEREBRAL CONDUCTION SPEED AND MITOCHONDRIAL FUNCTIONING

CROSS-REFERENCE TO RELATED APPLICATIONS

The present application claims priority of U.S. Application No. 63/084,643, filed Sep. 29, 2020, the entire contents of which is hereby incorporated by reference.

BACKGROUND

Field

Methods to improve neural stimulation by applying a biphasic waveform with anodal-first component to increase the speed of conduction and improve mitochondrial function.

Description of the Related Art

Cerebellar disorders typically manifest with ataxia-incoordination of movement, instability of gait, impairment of articulation, and difficulty with eye movement and swallowing. It has become apparent recently that many cerebellar patients also experience changes in intellect and mood. The field of non-invasive brain stimulation has made much progress in the development of specific stimulation protocols to modulate cerebellar excitability and try to restore the physiological activity of the cerebellum in patients with ataxia. Non-invasive brain stimulation protocols have emerged, employing transcranial direct current stimulation (tDCS) techniques.

With regard to cerebral stimulation, stimulators are built similar to cardiac stimulators, that is, they have short pulse widths and can produce biphasic (cathodal/anodal) waveforms. Changing to an anodal/cathodal sequence would, for example, enable stimulation of the most distant brain structures allowing burst pacing to stop epileptic seizures, and improving mitochondrial function whose impairment is associated with numerous serious brain disorders.

Accordingly, it is one object of the present disclosure to provide methods and systems for stimulating cell tissue by applying biphasic waveforms including a positive anodal pulse followed by a negative cathodal pulse.

SUMMARY

Methods and systems are described for stimulating cell tissues by applying biphasic waveforms including a positive anodal pulse followed by a negative cathodal pulse. The cell tissue may include nerve fibers, organs and skin.

In an exemplary embodiment of the present disclosure, a method of healing skin wounds is described, comprising guiding cell migration at the skin wound by applying biphasic waveforms including a positive anodal pulse followed by a negative cathodal pulse to the wound.

In a further exemplary embodiment, a method for interrupting epileptic seizures is described, comprising applying biphasic waveforms including a positive anodal pulse followed by a negative cathodal pulse to nerves to stimulate distal brain structures.

In another exemplary embodiment, a method for improving mitochondrial function in Alzheimer's disease is described, comprising applying biphasic waveforms including a positive anodal pulse followed by a negative cathodal pulse to nerves to stimulate distal brain structures.

In yet another exemplary embodiment, a method for stimulating hormone secreting cells is described, comprising applying biphasic waveforms including a positive anodal pulse followed by a negative cathodal pulse via electrodes located in a conduction pathway of a hormone secreting organ.

In an exemplary embodiment, a method for stimulating the release of insulin from the pancreas is described, comprising applying biphasic waveforms including a positive anodal pulse followed by a negative cathodal pulse via electrodes located in a conduction pathway of the pancreas.

In a further exemplary embodiment of the present disclosure, a method of lowering the membrane potential (MP) of a cell below the resting membrane potential (RMP) is described, comprising changing the cell membrane permeability by stimulating electrodes contacting an electric conduction pathway of the cell with a positive anodal pulse followed by a negative cathodal pulse.

In an exemplary embodiment of the present disclosure, a method for improving mitochondrial function in glutan ataxia is described, comprising applying biphasic waveforms including a positive anodal pulse followed by a negative cathodal pulse to nerves to stimulate distal brain structures.

In another exemplary embodiment of the present disclosure, a method for improving mitochondrial function in spinocerebellar ataxia is described, comprising applying biphasic waveforms including a positive anodal pulse followed by a negative cathodal pulse to nerves to stimulate distal brain structures.

In an exemplary embodiment of the present disclosure, a system for stimulating nerves is described, comprising a pulse generator configured to generate biphasic waveforms including a positive anodal pulse followed by a negative cathodal pulse; electrodes connected to the pulse generator by wires, wherein the electrode are configured to be connected to a nerve conduction pathway; and a programmable computing unit connected to the pulse generator, wherein the programmable computing unit includes circuitry and program instructions stored therein that, when executed by one or more processors, cause the one or more processors to signal the pulse generator to generate the biphasic waveforms.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1A:
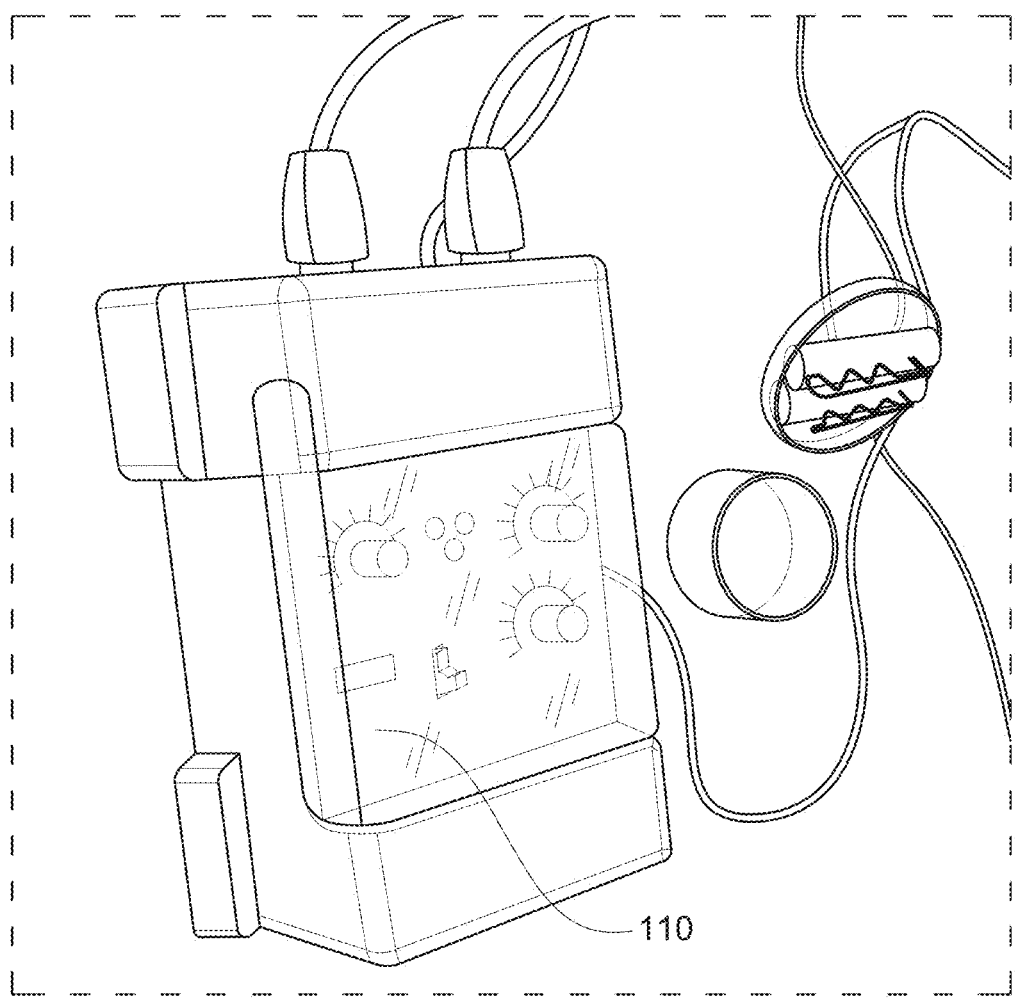
FIG. 1A depicts an external cardiac pacemaker.

Referring now to the drawings, wherein like reference numerals designate identical or corresponding parts throughout the several views.

Aspects of the present disclosure describe methods, devices and systems to improve neural stimulation by applying a biphasic waveform with anodal-first component to speed conduction and improve mitochondrial function in conditions such as cerebellar dysfunction (such as gluten ataxia, spinocerebellar ataxia, and Alzheimer's disease). Improved neural stimulation of more distal brain structures may interrupt epileptic seizures. Additionally, biphasic waveforms including a positive anodal pulse followed by a negative cathodal pulse speed wound healing by lowering the cell membrane potential of the skin, and may stimulate the release of hormonal secretions or insulin by proper placement of electrodes.

Experiments in the isolated Langendorff rabbit heart showed that a biphasic packing pulse produced an evoked response that conducted at a faster velocity through the myocardium and resulted in increased ventricular contractility when compared to a monophasic cathodal pulse. The mechanism of these changes was thought to be due to recruitment of a higher number of voltage-sensitive sodium channels, which in turn increased intracellular calcium concentration.

Applied electric fields may have a potential clinical role in guiding cell migration in wound healing. The magnitude and direction of the electric field can be more precisely and quickly changed than most other guidance cues such as chemical cues.

The impact of varying waveforms on cellular activity may have potential uses in hormone excreting cells, neural and gastric tissues.

Paced monophasic and biphasic waveforms have been shown to alter transmembrane potentials and the metabolism of human fibroblasts. The resting transmembrane potential (TMP) of primary human fibroblast cells was altered in predictable directions by subjecting cell cultures to specific monophasic and biphasic waveforms. Cells electrically stimulated with an anodal pulse resulted in hyperpolarization while a cathodal waveform depolarized the TMP to below that of non-paced control cells. The biphasic waveform, consisting of an anodal pulse followed immediately by an inverse symmetric cathodal pulse, also lowered the TMP similar to that of the cathodal pulse. The effect of short-term pacing on the TMP can last up to 4 hours before the potentials equilibrate back to baseline. While subjecting the cells to this electrical field stimulation did not appear to damage the integrity of the cells, the three paced electrical stimulation waves inhibited expansion of the cultures when compared to non-paced control cells. With longer pacing treatments, elongation of the cells and electrotaxis towards the anodal polarity were observed. Pacing the fibroblasts also resulted in modest, yet very statistically significant changes to cellular adenosine-5'-triphosphate (ATP) levels, and cells undergoing anodal and biphasic (anodal/cathodal) stimulation also exhibited altered mitochondrial morphology. The application anodal electrical currents to cells was shown to affect cellular metabolism and function of the cells.

All live cells have a stable transmembrane potential (TMP) voltage differential across the cell membrane when the cell is at rest. This is the result of the accumulated ion concentrations within the cell compared to that outside the membrane. Electrically active cells, such as neurons, muscles, and pancreatic beta cells, are called excitable because they can produce an action potential due to a short-lived rapid depolarization of the TMP before returning to the higher resting state. These cells achieve this by expressing fast-acting voltage gated ion channels that allow the very rapid exchange of ions across the cellular membrane. While calcium and chloride ions make distinct contributions, it is particularly the sodium (Na+) and potassium (K+) which contribute most to this ion concentration potential.

Even cells that do not generate action potentials need to maintain a TMP voltage differential in order to enable secondary active transport of metabolites. Non-excitable cells use slower membrane ion exchange pumps or transporters to move charges across the membrane, often in conjunction with the transport of a metabolite. Most of these transporters require a concentration gradient, a supply of energy, and are considerably slower than the fast-acting ion channels of the excitable cells.

Alterations to membrane potential are carefully modulated by ion channels within the cell membrane to maintain homeostasis. Subjecting cells to pacing waveforms alters the TMP since it results in a manipulation of these charged ions. Electrically altering the TMP can then have profound effects on cellular physiology in terms of both metabolism and function.

Experiments were conducted on different types of cells using anodal, cathodal, biphasic anodal/cathodal waveforms and compared with non-paced cells.

Figure 1B:
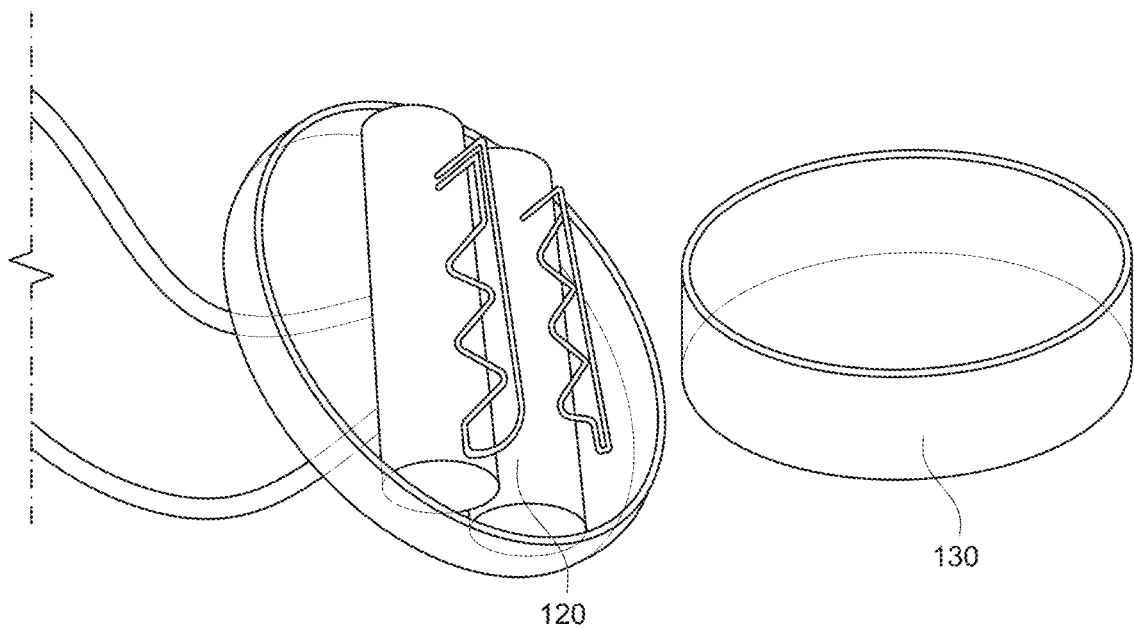
FIG. 1B depicts electrodes and cell containers.
Figure 1C:
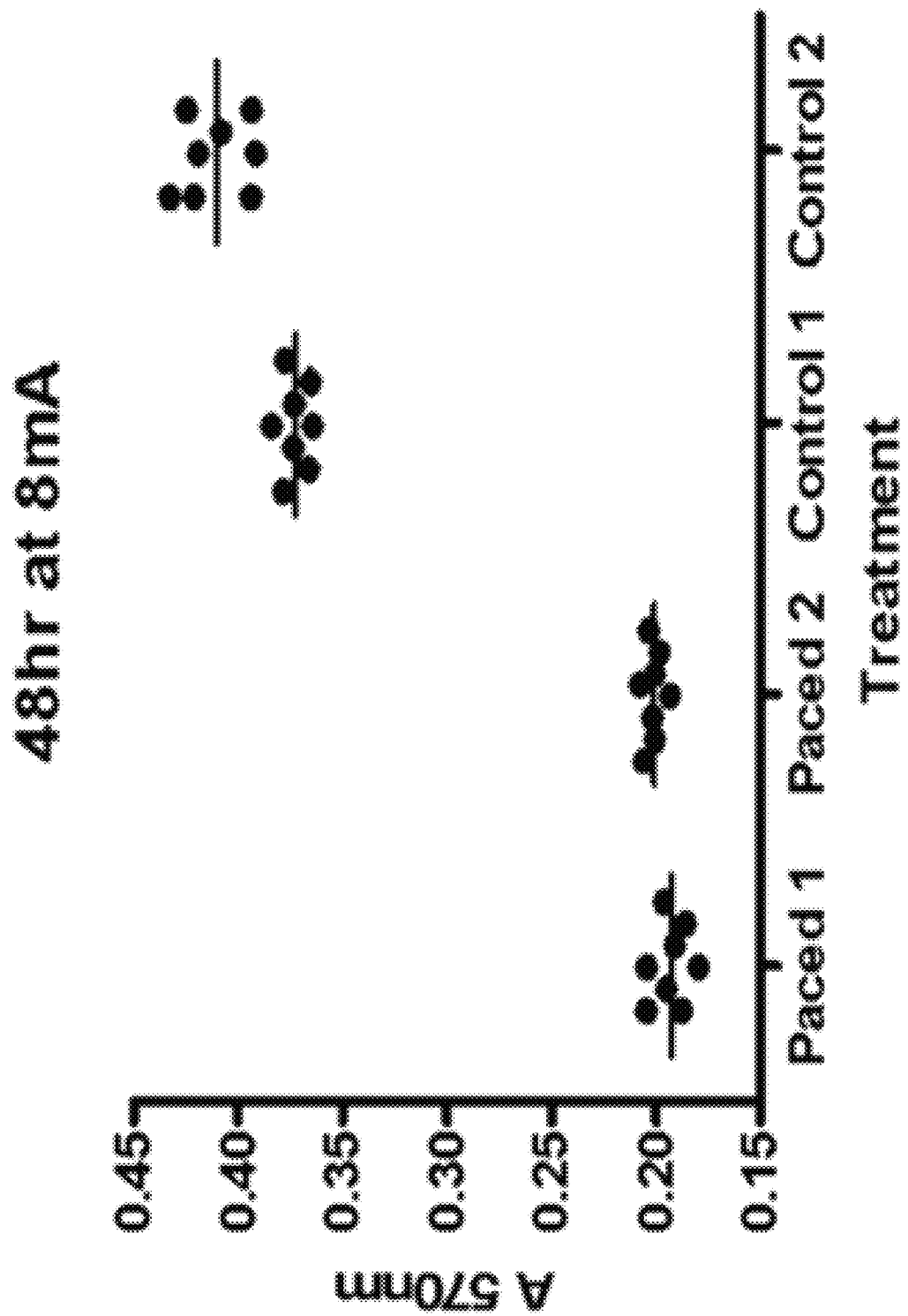
FIG. 1C shows the changes in length due to anodal pacing at 8 mA for two cultures and for two unpaced control groups.

FIG. 1A shows an external cardiac pacemaker 110 connected to electrodes which are applied to cell cultures. The pacemaker was set at 5 V magnitude 1.8 ms corresponding to an output of 10 mA at a rate of 1.7 Hz which was used as the input signal to a slave simulator. The slave simulator produced the actual monophasic anodal and cathodal and biphasic anodal/cathodal pulsed square waveforms used for stimulation. In non-limiting examples, the external pacemaker may be obtained from Pace Medical, Inc., Waltham, Mass., U.S.A. and the slave simulator may be a model 71006, obtained from Rivertek Medical Systems, Minneapolis, Minn., U.S.A. The monophasic waveforms were ±5.0 V at 1.8 ms. The biphasic waveform was defined as a +2.5 V at 0.9 ms anodal pulse immediately followed by a −2.5 V at 0.9 ms cathodal pulse. FIG. 1B shows the electrode structure 120 which was used in the experiments. The cells (dish 130) used in the experiment were human foreskin tissues which were dyed with 3,3'-dipropylthiadicarbocyanine iodide (DisC3-5) dye. The cells were paced for 48 hours at 8 m amps. FIG. 1C shows the changes in membrane potential due to anodal pacing at 8 mA for two cultures and for two unpaced control groups, where a lower height represents higher membrane potential.

Figure 2A:
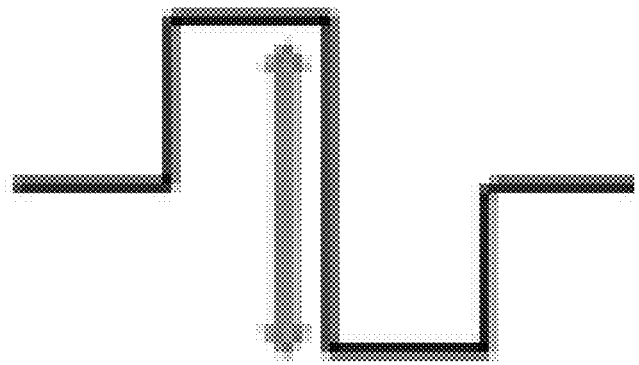
FIG. 2A depicts a biphasic anodal/cathodal waveform.
Figure 2B:
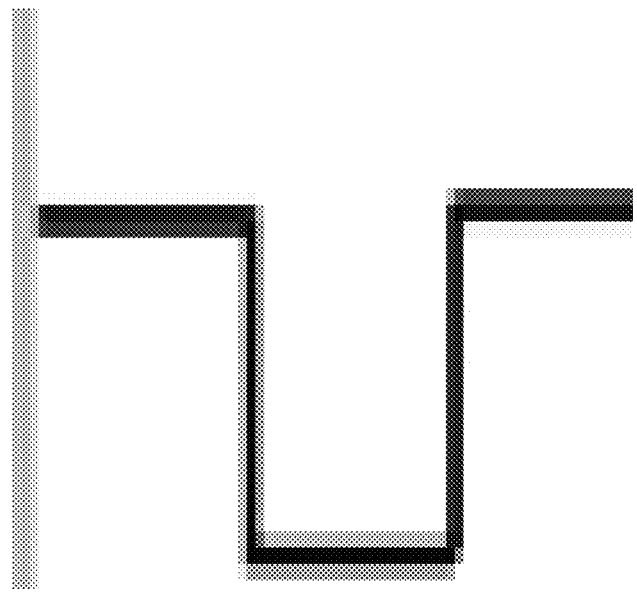
FIG. 2B depicts a cathodal only waveform.
Figure 2C:
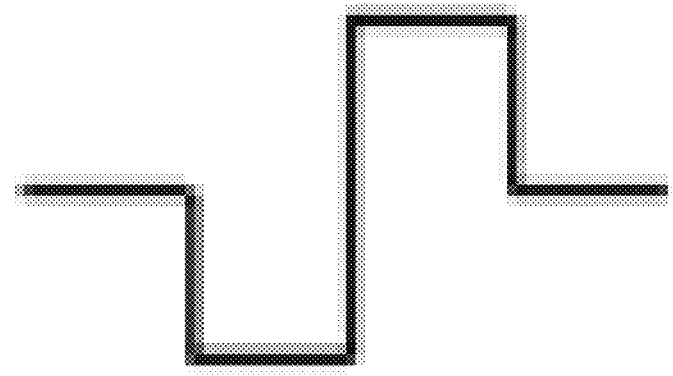
FIG. 2C depicts a biphasic cathodal/anodal waveform.

FIG. 2A shows a biphasic anodal/cathodal waveform. The vertical arrow shows the change in amplitude between the maximum positive and the maximum negative amplitudes. FIG. 2B shows a cathodal only pulse. FIG. 2C shows a biphasic cathodal/anodal waveform.

Figure 3:
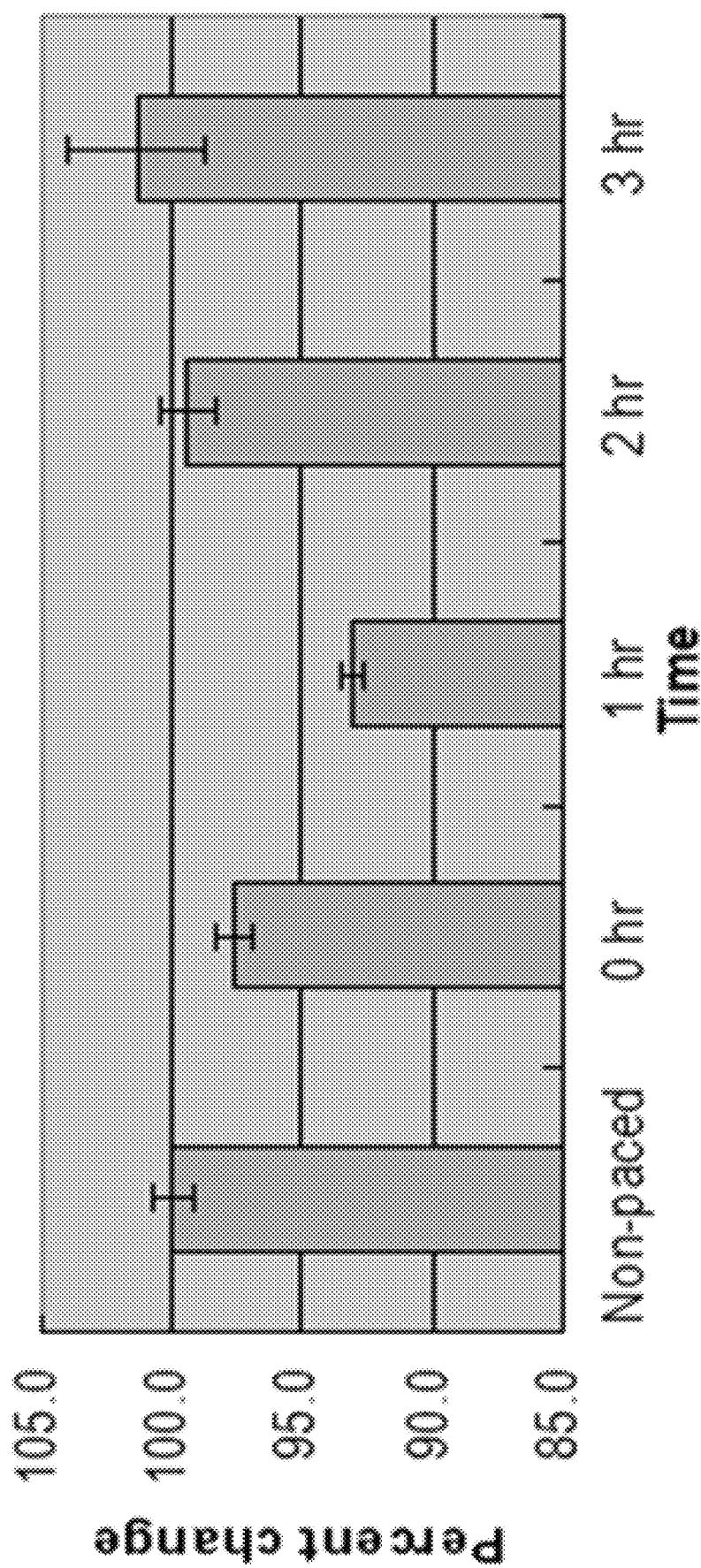
FIG. 3 shows the time duration of the percent change in resting membrane potential (RMP) over time for rat pancreas/islet cell tumor tissue cells.

FIG. 3 shows the time duration of the percent change in resting membrane potential (RMP) over time for rat pancreas/islet cell tumor tissue cells (CRL-2057 cells available from ATCC, P.O. Box 1549m Manassas, Va., U.S.A). The first histogram box represents the control group of non-paced cells. The zero hour histogram box represents the membrane potential of the paced cells immediately after anodal pacing, the 1, 2 and 3 hour histogram boxes represent the membrane potentials after 1, 2, and 3 hours respectively. The percent change in the membrane potential is greatest three hours after pacing. These results show that the effect of the pacing lasts and increases over time. Table 1 shows the mean percent change and standard error of the mean (s.e.m.) of the results of FIG. 3.

TABLE 1

Time duration of increased membrane potential

| | Non-paced | 0 hr | 1 hr | 2 hr | 3 hr |
|---|---|---|---|---|---|
| Mean | 100 | 96.7 | 93.1 | 99.4 | 102.4 |
| S.E.M | 0.78 | 0.76 | 0.45 | 1.07 | 2.69 |

Figure 4:
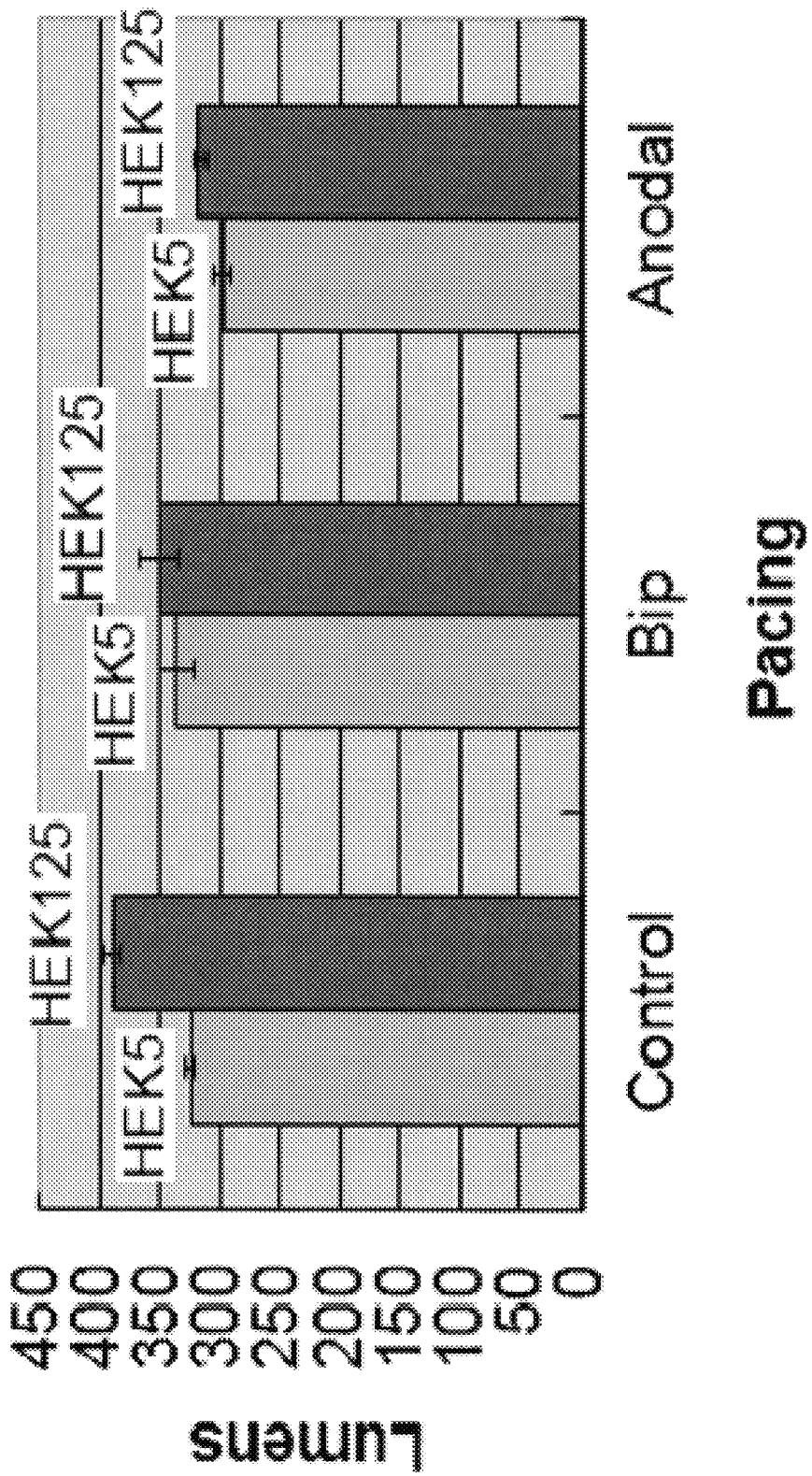
FIG. 4 shows the resting membrane potential after pacing for two hours using a biphasic waveform and an anodal only pulse for human embryonic kidney (HEK) cells.

FIG. 4 shows the resting membrane potential after pacing for two hours using a biphasic waveform and an anodal only pulse. A control group is also shown. The cells were human embryonic kidney (HEK) cells. Two different cells were used, HEK5 and HEK125 for comparison. HEK5 showed increased RMP for biphasic anodal/cathodal pacing and decreased RMP for anodal only pacing as compared to the control group. HEK125 showed decreased RMP for biphasic anodal/cathodal pacing and further decreased RMP for anodal only pacing as compared to the control group.

Figure 5A:
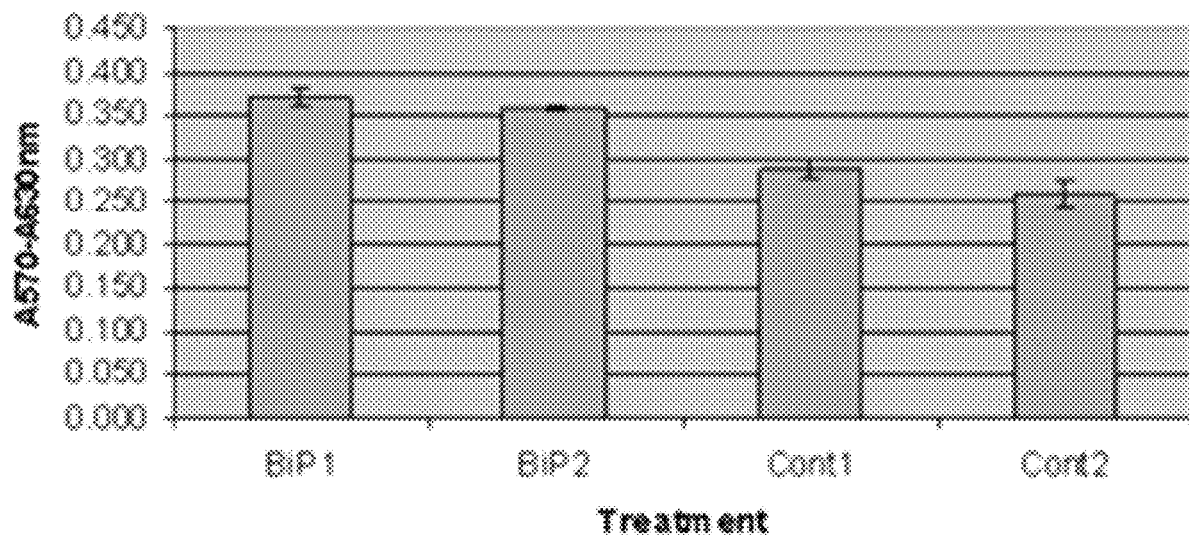
FIG. 5A shows a first MTT cell viability assay.
Figure 5B:
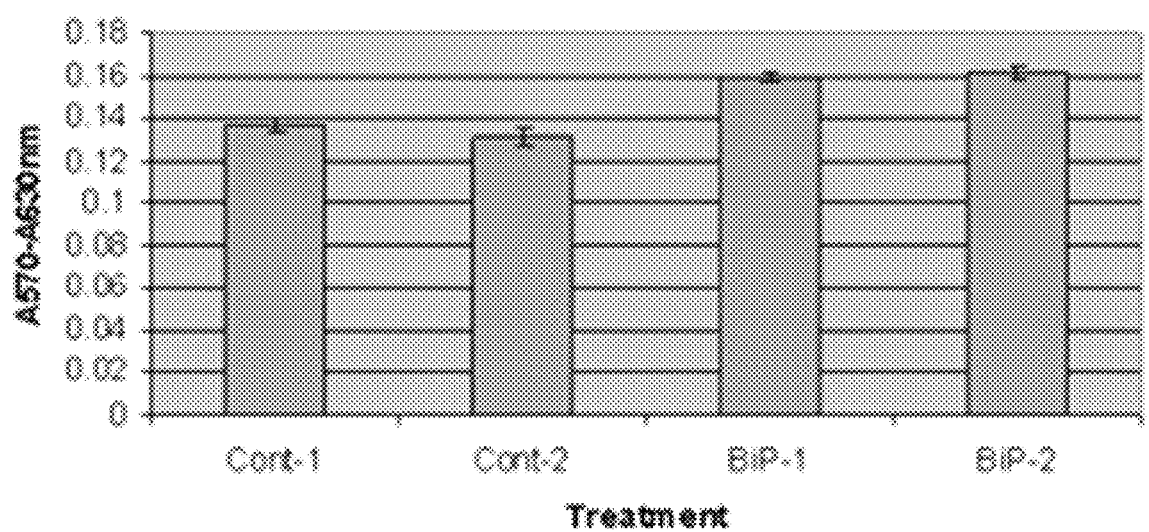
FIG. 5B shows a second MTT cell viability assay.

FIG. 5A and FIG. 5B shows two separate MTT cell viability experiments, each using two controls and two sets of cells. The MTT cell viability (or proliferation of the cells was measured. The MTT assay is used to measure cellular metabolic activity as an indicator of cell viability, proliferation and cytotoxicity. This colorimetric assay is based on the reduction of a yellow tetrazolium salt (3-(4,5-dimethylthiazol-2-yl)-2,5-diphenyltetrazolium bromide or MTT) to purple formazan crystals by metabolically active cells. The viable cells contain NAD(P)H-dependent oxidoreductase enzymes which reduce the MTT to formazan. The insoluble formazan crystals are dissolved using a solubilization solution and the resulting colored solution is quantified by measuring absorbance at 500-600 nanometers using a multi-well spectrophotometer. The darker the solution, the greater the number of viable, metabolically active cells. FIG. 5A shows that the biphasic anodal/cathodal pacing over 7 days of the BIP1 and BiP2 cells resulted in significantly greater absorbance than for the unpaced Cont1 and Cont2 groups. FIG. 5B again shows that the that the biphasic anodal/cathodal pacing over 7 days of the BIP1 and BiP2 cells resulted in significantly greater absorbance than for the unpaced Cont1 and Cont2 groups.

Electrical stimulation on insulin release from rat insulinoma (INS-1) cells was studied. Anodal/cathodal biphasic stimulation (ACBPS) resulted in a voltage and stimulation duration dependent increase in insulin release. ACBPS elicited insulin release both in the presence and absence of glucose. Basal and ACBPS-induced insulin secretion could be inhibited by mitochondrial poisons and calcium channel blockers, indicating that insulin release was dependent on adenosine triphosphate (ATP) and the influx of calcium. ACBPS parameters that released insulin caused no detectable plasma membrane damage or cytotoxicity, although temporary morphological changes could be observed immediately after ACBPS. ACBPS did not alter the plasma membrane transmembrane potential but did cause pronounced uptake of a red-fluorescent dye (MitoTracker Red) that stains mitochondria in live cells with accumulation dependent upon membrane potential. While the ATP:ADP ratio after ACBPS did not change, the guanosine triphosphate (GTP) levels increased and increased GTP levels have previously been associated with insulin release in INS-1 cells. These results provide evidence that ACBPS can have significant biological effects on cells. In the case of INS-1 cells, ACBPS promotes insulin release without causing cytotoxicity.

Electrical field stimulation has historically been used to elicit responses in isolated tissues mediated by the activation of intrinsic nerves. The vulnerability of such responses to inhibition by tetrodotoxin has been used to define their neural origin. Depending on the species, pancreatic islets can be innervated by cholinergic and adrenergic nerves with their neurotransmitters having opposing effects on insulin secretion. Electrical field stimulation of fragments of rat pancreas induced the release of insulin that primarily involved activation of intrinsic cholinergic nerves, as demonstrated by its vulnerability to inhibition by atropine Electrical field stimulation may also be used to elicit direct depolarization of cells. In addition, its use is expanding into tissues that are not normally considered to be electrically excitable.

In some embodiments, electrical stimuli can be delivered as either monophasic or biphasic waveforms, and with anodal as well as cathodal polarities.

In another embodiment, a pulse generator can combine pulses so that the biphasic anodal followed by cathodal pulses are continuously generated as a train of pulses, similar to an AC pulse.

Since an AC signal can be viewed as just combinations of biphasic pulses strung together, in another embodiment a low voltage AC signal can be used to precondition the nerves. The low voltage AC signal may precondition the nerve cells and may be followed by an anodal or cathodal stimulation pulse.

Figure 6A:
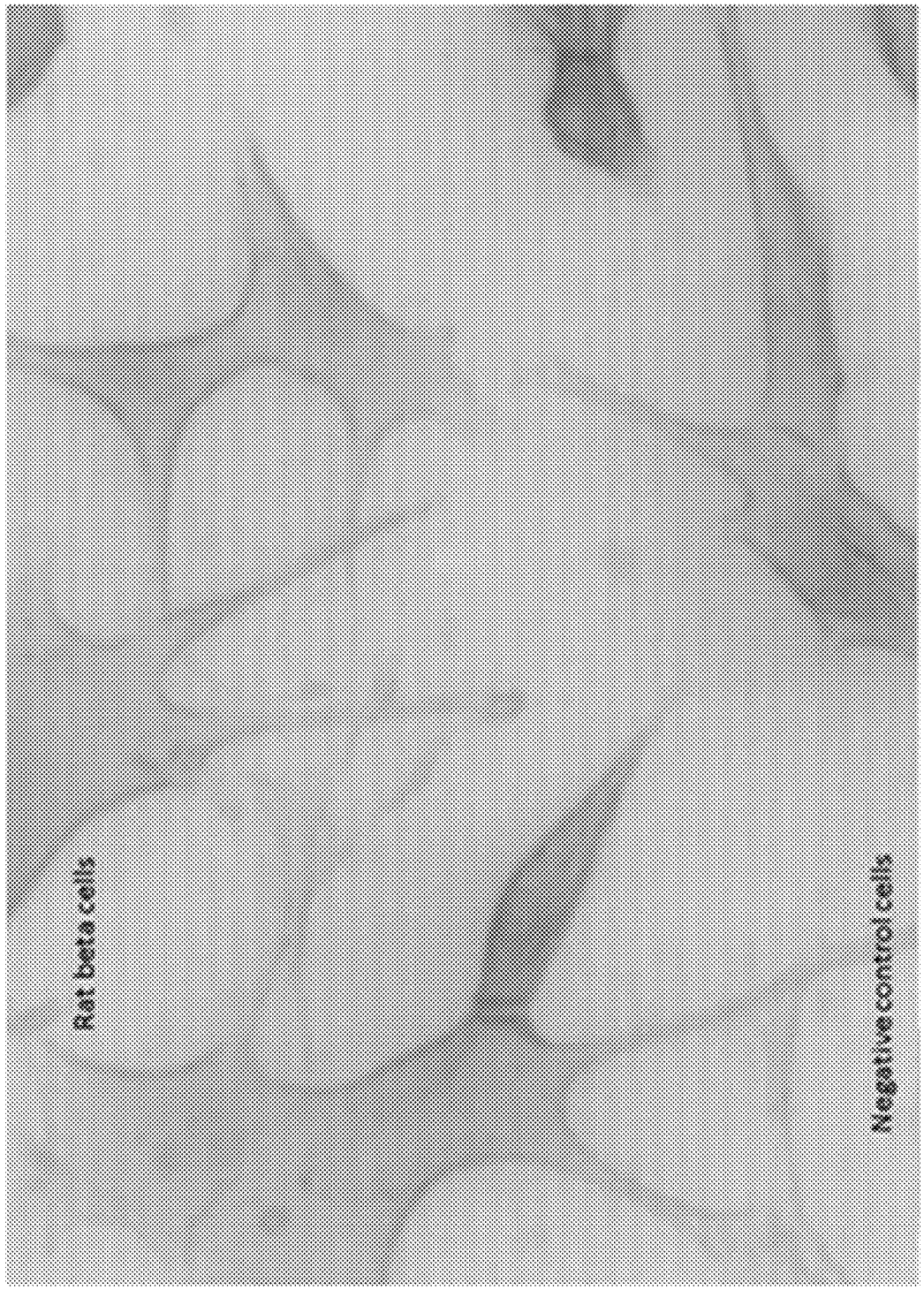
FIG. 6A shows a control group in biphasic anodal/cathodal stimulation of rat beta cell mitochondria stained with a red-fluorescent dye with accumulation dependent upon membrane potential.
Figure 6B:
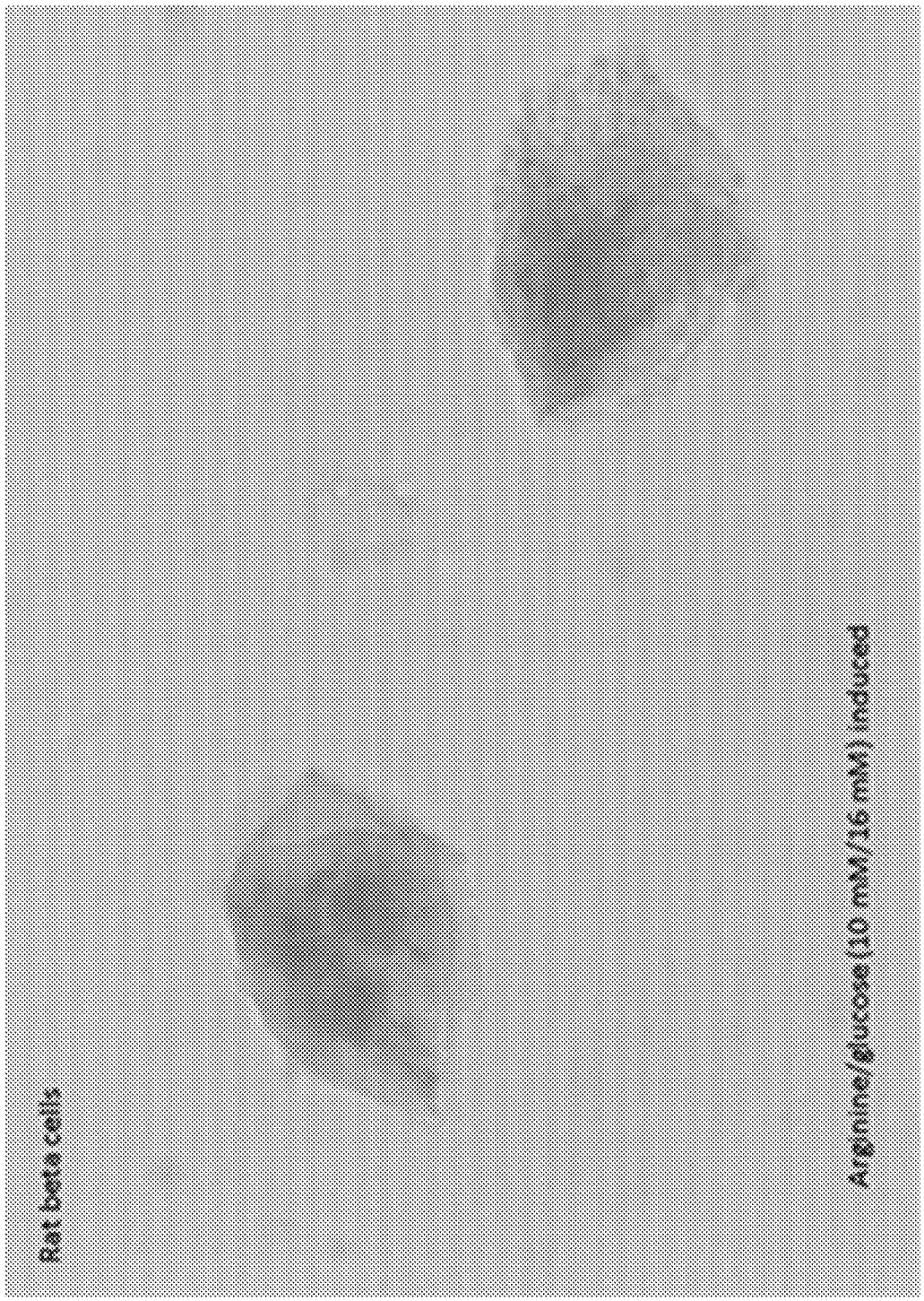
FIG. 6B shows biphasic anodal/cathodal stimulation of rat beta cell mitochondria stained with a red-fluorescent dye with accumulation dependent upon membrane potential in which arginine/glucose was induced.
Figure 6C:
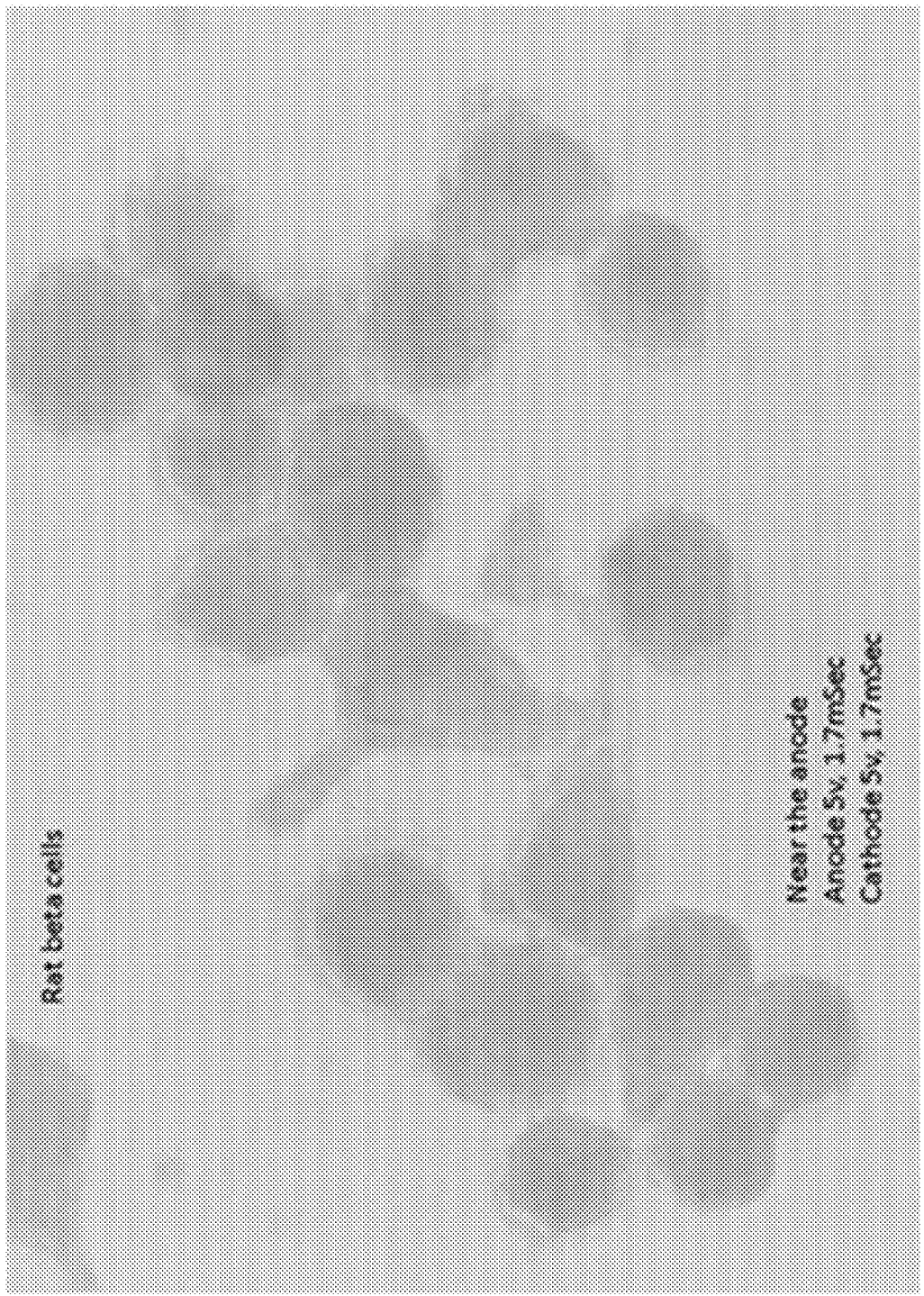
FIG. 6C shows cells near the anode receiving biphasic stimulation of 5V anode and 5V cathode for 1.7 milliseconds.
Figure 6D:
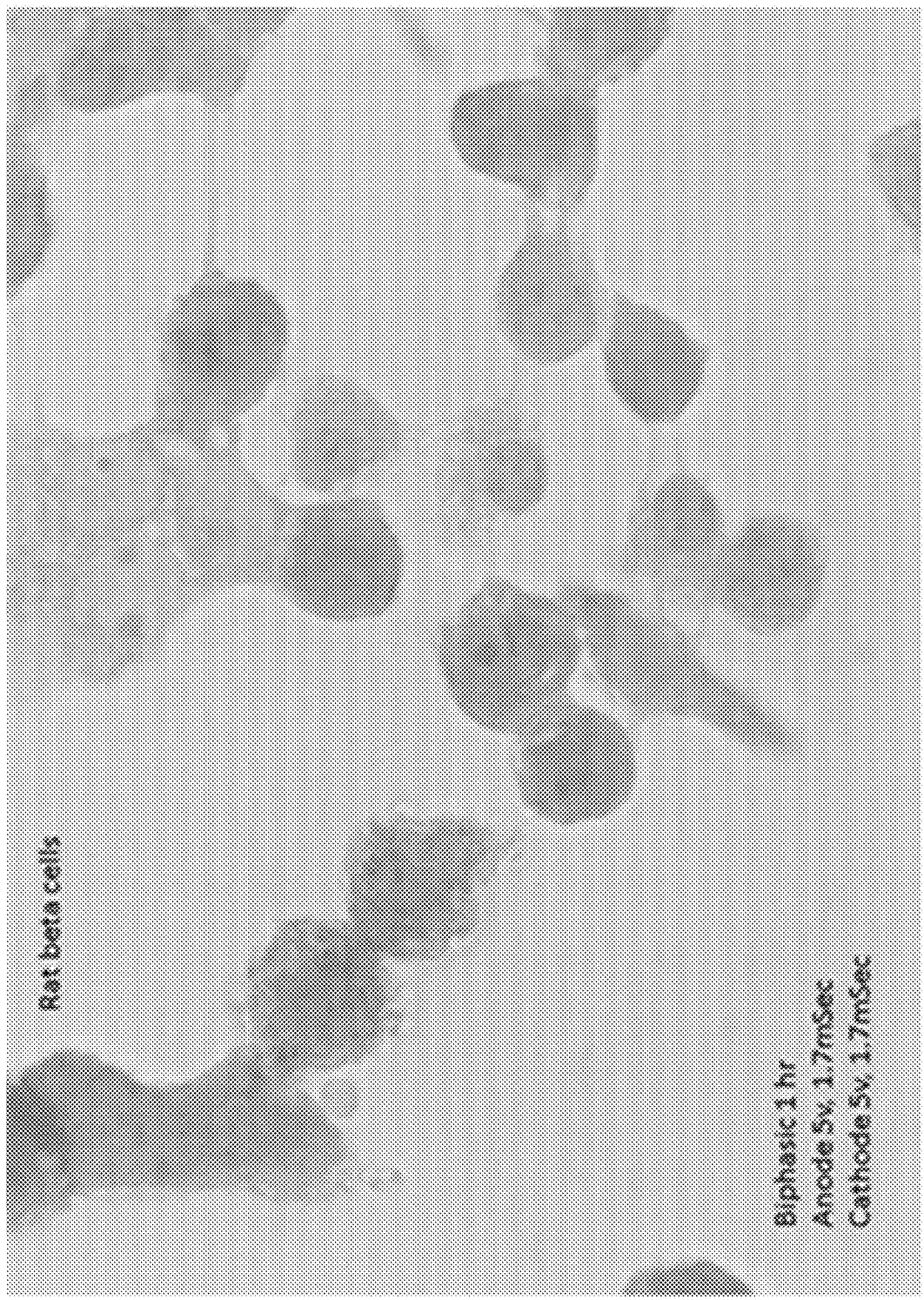
FIG. 6D shows the uptake of the red dye indicating high membrane potential from receiving biphasic stimulation.

FIG. 6A-6D show insulin production due to biphasic anodal/cathodal stimulation of rat beta cells stained with the red-fluorescent dye (MitoTracker Red) which stained the mitochondria in the live cells with accumulation dependent upon membrane potential. FIG. 6A is the control group. FIG. 6B shows that arginine/glucose (10 mM/16 mM) was induced. FIG. 6C shows the cells near the anode receiving biphasic stimulation of 5V anode and 5V cathode for 1.7 milliseconds. FIG. 6D shows the uptake of the red dye indicating high membrane potential from receiving biphasic stimulation of 5V anode and 5V cathode for 1.7 milliseconds.

Table 2 shows the results from an enzyme-linked immunosorbent assay (ELISA) for rat insulin. The absorption at 450 nm was measured for two cell sets. The third column shows the average absorption. These results show that the anodal pulse had the greatest effect on the release of insulin in the rat cells.

TABLE 2

ELISA for rat insulin

| Media | A450 nm | A450 nm | Avg. | BGD Corr. | Insulin ng/ml |
|---|---|---|---|---|---|
| control | 0.0519 | 0.0538 | 529 | 0 | 0 |
| anodal | 0.124 | 0.1498 | 0.1369 | 0.0841 | 0.2651 |
| cathodal | 0.0527 | 0.054 | 0.0534 | 0.0005 | 0.0016 |

CRL 2057 (rat pancreas islet cells) were paced for 3 hours in an adenine triphosphate assay. Triphosphate is involved in a variety of enzymatic reactions in maintaining normal life activities. When normal cells undergo apoptosis and necrosis, the content of ATP will be characteristically changed. Thus, ATP has been widely accepted as a valid marker of the viability of cells. The measurement of ATP using firefly luciferase is the most commonly applied method for estimating the number of viable cells.

Figure 7:
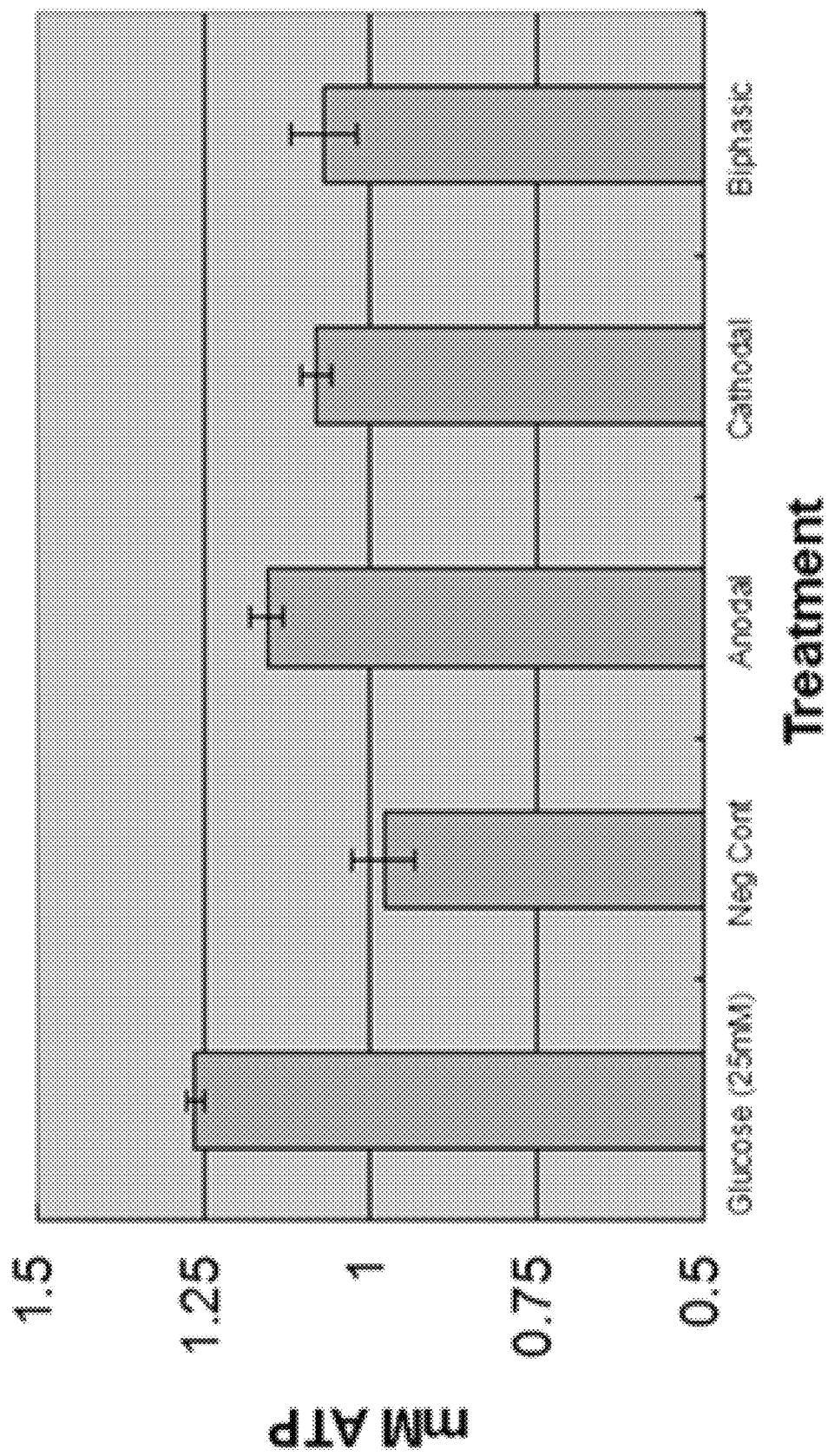
FIG. 7 shows an ATP assay of rat pancreas islet cells subjected to anodal, cathodal and biphasic electrical stimulation for 3 hours.

The ATP cell viability assay utilizes luciferase to catalyze the formation of light from ATP and D-luciferin, which can be measured with a luminometer or Beta Counter. The advantage of an ATP assay is that no incubation step is needed with a population of viable cells to convert a substrate (such as tetrazolium and resazurin) into a colored compound. There is also no need to remove cell culture medium or wash cells before adding the reagent, which can be fully automatic for high throughput. In FIG. 7, rat pancreas islet cells were subjected to anodal, cathodal and biphasic electrical stimulation for 3 hours in an ATP assay. These results are compared to glucose and negative control groups. Glycerol was phosphorylated and read by a UV spectrometer at 570 nm. The anodal, cathodal and biphasic groups all had significantly greater amounts of adenine triphosphate than did the negative control group, showing that the anodal, cathodal and biphasic groups had greater cell viability than did the control group.

Table 3 shows the actual measurements of the ATP assay of FIG. 7.

TABLE 3

ATP assay of rat pancreas cells with pacing.

| | Glucose | Neg Cont | Anodal | Cathodal | Biphasic |
|---|---|---|---|---|---|
| Mean | 1.26 | 0.98 | 1.16 | 1.08 | 1.07 |
| S.E.M. | 0.013 | 0.048 | 0.024 | 0.023 | 0.048 |

Figure 8:
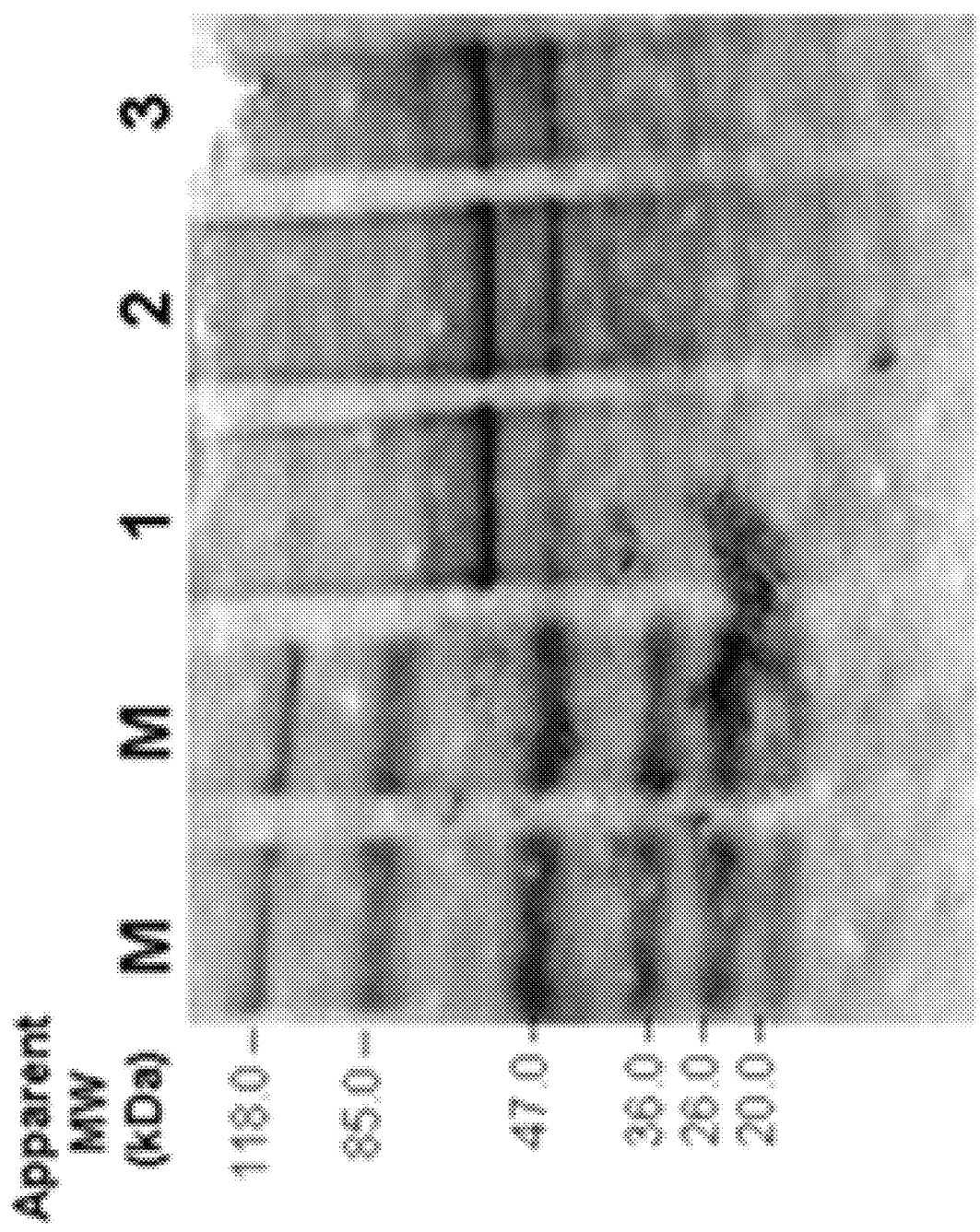
FIG. 8 shows a protein expression array of protein gel subjected to biphasic anodal/cathodal stimulation.

A protein expression gel array was subjected to a biphasic anodal/cathodal waveform to observe any overt changes in protein expression as a result of pacing. FIG. 8 shows the results of electrical stimulation of the gel array. In FIG. 8, each strip "M" is a control group with no stimulation. "1", "2" and "3" represents gels which have undergone anodal, cathodal and biphasic (anodal followed by cathodal) stimulation respectively. The channels of darker color represent intra-cellular protein arrays separated by mobility (molecular weight plus electrical charge). This shows that each electrical waveform has a different effect, which is an unexpected result.

Figure 9A:
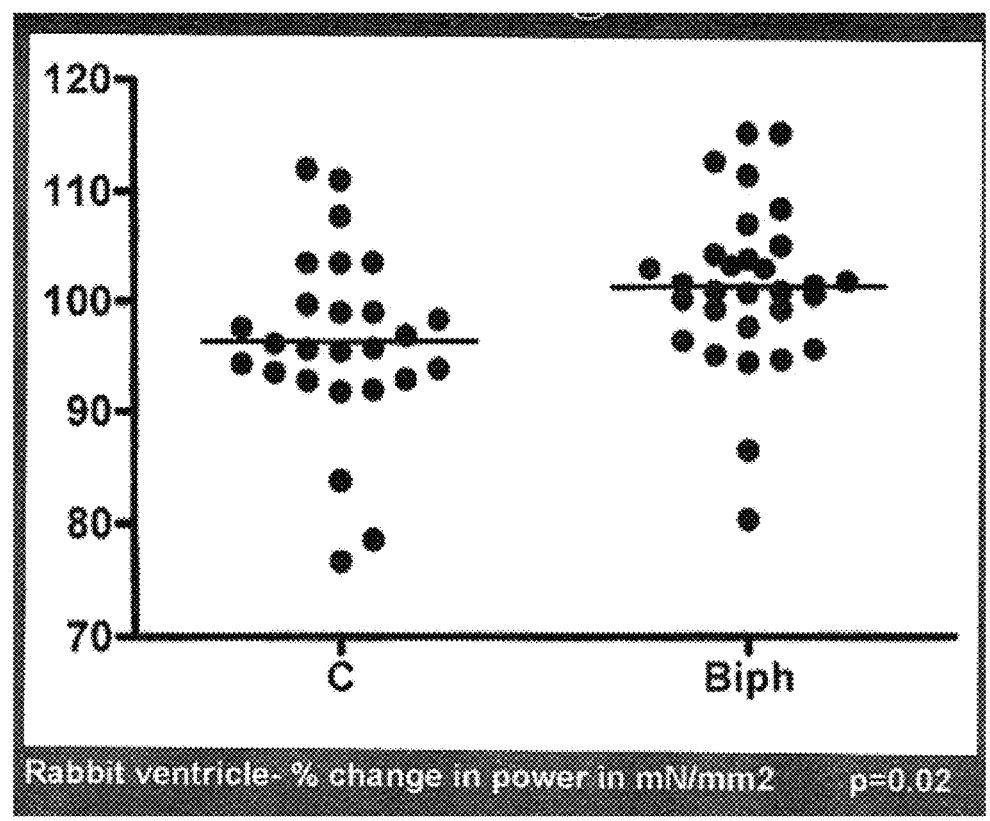
FIG. 9A shows the change in contractility in isolated muscle strips of a rabbit ventricle due to cathodal (left) and biphasic (right) pulses.
Figure 9B:
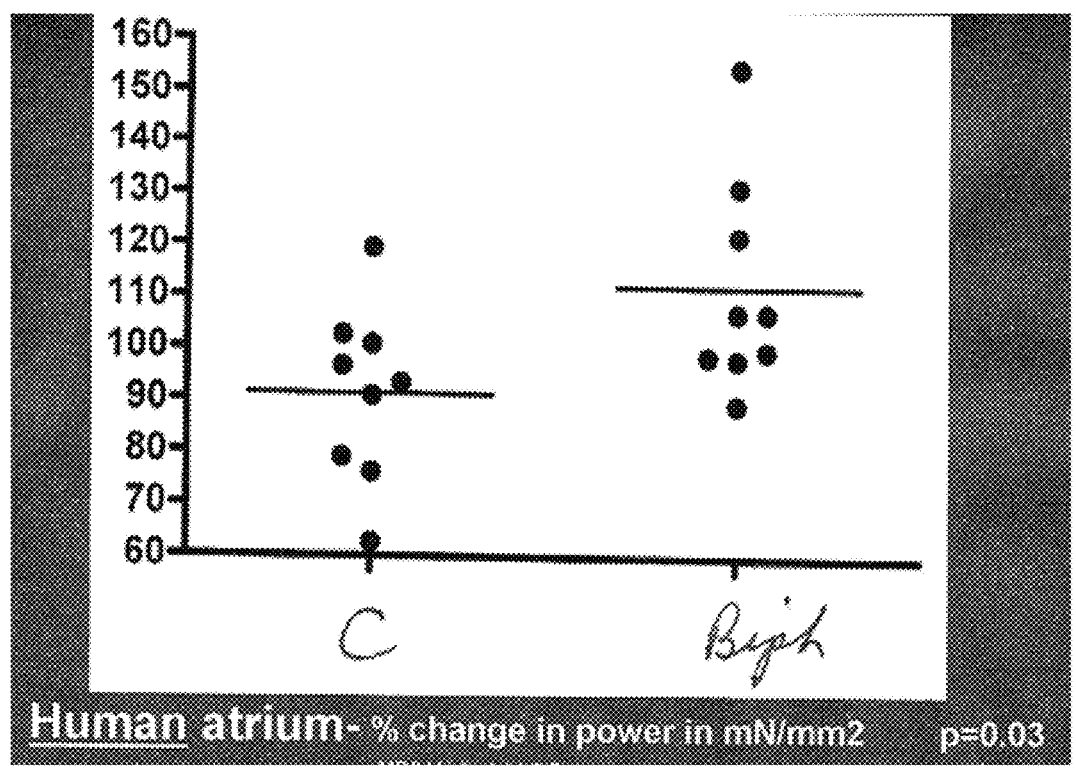
FIG. 9B shows the change in power in isolated muscle strips of a human atrium due to cathodal (left) and biphasic pulses (right).

FIG. 9A shows the change in contractility in isolated muscle strips of a rabbit ventricle due to cathodal (left) and biphasic (right) pulses and FIG. 9B shows the change in power in isolated muscle strips of a human atrium due to cathodal (left) and biphasic pulses (right). In both figures, the biphasic pulse resulted in higher contractility of the muscle strip.

Research in cardiac pacing performed on pigs which compared the contractility and relaxation due to cathodic only and biphasic cathodal/anodal waveforms demonstrated that the biphasic waveform increased contractility and relaxation. Upstroke (dP/dt+) and relaxation (dP/dt2) of left ventricular pressure curve were measured in two 50 kg subjects paced slightly above intrinsic rate with cathodal (C) and anodal followed by cathodal biphasic (B) pacing pulses.

Biphasic and monophasic electrical stimulation has been shown to affect mitochondrial dynamics, cell apoptosis, and cell proliferation. Aspects of the present disclosure compare the effects of monophasic and biphasic, anodal, and cathodal electrical stimulation (ES) on apoptosis, proliferation, and mitochondrial dynamics in neuroblastoma SH-SY5Y cells. The cells were cultured and treated with ES. An alamar blue assay was performed to measure cell proliferation. The protein expression of apoptotic-related proteins Bcl-2 associated X (Bax), B cell lymphoma 2 (Bcl-2), optic-atrophy-1 (OPA1), mitofusin2 (Mfn2), phosphorylated dynamin-related protein 1 at serine 616 (p-DRP1), and total dynamin-related protein 1 (Total-DRP1) were also determined. The results showed that monophasic anodal and biphasic anodal/cathodal (Bi Anod) ES for 1 hr at 125 pulses per minute (2.0 Hz) produced the most significant increase in cell proliferation. In addition, monophasic anodal and Bi Anod ES treated cells displayed a significant increase in the levels of anti-apoptotic protein Bcl-2, whereas the Bax levels were not changed. Moreover, the levels of Mfn2 were increased in the cells treated by Bi Anod, and OPA1 was increased by monophasic anodal and Bi Anod ES, indicating increased mitochondrial fusion in these ES-treated cells. However, the levels of mitochondrial fission indicated by DRP1 remained unchanged compared with non-stimulated cells. These findings were confirmed through visualization of mitochondria using Mitotracker Deep Red, demonstrating that monophasic anodal and Bi Anod ES could induce pro-survival effects in SH-SY5Y cells through increasing cell proliferation and mitochondrial fusion.

The human organism is composed of multiple cells, all of which have different components and therefore with different resting membrane potentials (RMP). Some of these cells are excitable (e.g.: cells; neurons; muscle fibers), generating an action potential when subjected to an external stimulus, causing its membrane depolarization. The resting membrane potential (RMP) is due to changes in membrane permeability for potassium, sodium, calcium, and chloride, which results from the movement of these ions across it. Once the membrane is polarized, it acquires a voltage, which is the difference of potentials between intra and extracellular spaces. RMP is created by the distribution of ions and its diffusion across the membrane. Potassium ions are important for RMP because of its active transport, which increase more its concentration inside the cell. However, the potassium-selective ion channels are always open, producing an accumulation of negative charge inside the cell. Its outward movement is due to random molecular motion and continues until enough excess negative charge accumulates inside the cell to form a membrane potential. Resting membrane potential varies according to types of cells. For example, skeletal muscle cells have an RMP of −95 mV, smooth muscle cells: −50 mV, astrocytes: −80/−90 mV, neurons: −70 mV and erythrocytes: −12 mV.

Aspects of the present disclosure describe lowering the membrane potential below the RMP by stimulating a cell with biphasic (positive) anodal pulse followed by a (negative) cathodal pulse to change the cell membrane permeability.

If one electrode is placed inside the axon and one to the cytoplasmic surface of the axon, hyperpolarization (in the case of negative internal electrodes) or depolarization (in the case of negative external) occurs. Increasing the membrane potential to the threshold potential (in a membrane with resting membrane potential, from −70 mV to about −55 mV), a nerve fiber responds with the emergence of an action potential (sudden opening of voltage-gated sodium ion channels, thus allowing ions of sodium to enter through the membrane, causing the inside of the cells to become positive. If the increment in the membrane potential does not reach the threshold potential, the sodium voltage-gated channel will not open. In this case, no action potential is generated. In the next phase, the membrane again becomes permeable to potassium ions and the potential returns to resting value despite a slight hyperpolarization.

Some applications of biphasic anodal/cathodal pacing (other than in cardiac pacing) are to speed conduction and improve mitochondrial function in conditions such as cerebellar dysfunction (such as gluten ataxia, spinocerebellar ataxia, and Alzheimer's disease), to improve neural stimulation of more distal brain structures to interrupt epileptic seizures, to guide cell migration at the skin to heal skin wounds, to stimulate hormone excreting cells, to stimulate release of insulin, and the like.

Experimentation in non-human animals of numerous species indicate that monophasic anodal and biphasic anodal/cathodal pacing stimuli increases speed of conduction (with 0.5 msec/0.5 msec in the rabbit heart from 12% to 34% depending on the direction of the depolarization and the distance from the stimulating electrode), and increases the contractility of the myocardium (with the change in pressure per unit time (dP/dt) increasing by 32%). Also, the membrane potential. ATP and other products of cellular metabolism were increased, and insulin release in cell cultures was controlled in a manner different from the usual glucose-dependent mechanism.

The effect of the biphasic anodal/cathodal pacing stimuli are theorized to be mediated by hyper-polarization of the cells prior to their actual depolarization. This is because this first anodal phase is non-stimulatory, but preconditions the tissue by increasing the membrane potential, so that when stimulation does occur on the "break" of the anodal coincident with the "make" of the cathodal phase, the depolarization occurs from a more electronegative point, the phase zero is steeper, more sodium rushes in, the depolarization is stronger, conduction speed is increased, more calcium is exchanged for the sodium and contractility is enhanced in addition to other intra-cellular effects.

Brain stimulation can be categorized into non-invasive brain stimulation and invasive brain stimulation. Invasive brain stimulation includes deep brain stimulation and invasive vagus nerve stimulation, whereas non-invasive brain stimulation includes transcranial direct current stimulation and transcranial alternating current stimulation. A deep brain stimulation system includes electrode leads, wires, and a pulse generator. Neurosurgeons implant electrode leads in the brain and pulse generator below the collar bone. Both are connected by wires which are tunneled underneath the skin.

Vagus nerve stimulation modulates brain network activity by stimulating the tenth cranial nerve. The stimulation of tenth cranial nerve (vagus nerve) can be performed using two methods: direct invasive stimulation and indirect transcutaneous non-invasive stimulation. The invasive system includes a pulse generator and electrodes. Surgeons attach electrodes to the left-side vagus nerve and connect them to a pulse generator which is implanted in the left thoracic region. The pulse generator delivers programmable electrical stimulation to the vagus nerve. Research has shown that both deep and non-invasive brain stimulation improved cognitive functions in patients with Alzheimer's disease.

Transcranial direct current stimulation delivers electric current, typically ranged 1 to 2 mA, through two or more electrodes placed on the scalp. Studies have shown that transcranial direct current stimulation improves cognitive functions in patients with Alzheimer's disease.

Transcranial alternating current stimulation delivers a current which oscillates above and below zero with a given stimulation strength (i.e., peak-to-peak amplitude) at a particular frequency. In transcranial direct current stimulation, the excitability thresholds of neuronal membrane potentials are modulated, whereas transcranial alternating current stimulation directly interacts with ongoing neuronal activity during cognitive or sensory-motor processes, leading to an entrainment or synchronization of brain network oscillations. Brain oscillations represent various brain functions. Because specific frequencies reflect particular ongoing cognitive or sensory-motor processes, transcranial alternating current stimulation may enhance ongoing processes through exogenous augmentation of those oscillations. Therefore, transcranial alternating current stimulation has the potential to synchronize frequency-specific neuronal networks, thereby causing behavioral changes.

Small trials have shown that transcranial alternating current stimulation can improve specific cognitive functions in healthy adults by directly interacting with ongoing oscillatory cortical activity. For example, a sham-controlled crossover trial of 24 healthy adults revealed that transcranial alternating current stimulation significantly improved retrieval accuracy. Therefore, transcranial alternating current stimulation may also have potential effects on patients with Alzheimer's disease.

An embodiment of the present disclosure describes healing skin wounds by the application of biphasic anodal/cathodal pulses to guide cell migration at the site of the wound.

An embodiment of the present disclosure describes interrupting epileptic seizures by applying biphasic anodal/cathodal waveforms to stimulate distal brain structures.

An embodiment of the present disclosure describes lowering the membrane potential below the RMP by stimulating a cell with biphasic (positive) anodal pulse followed by a (negative) cathodal pulse to change the cell membrane permeability.

Another embodiment describes improving mitochondrial function in glutan ataxia by the application of biphasic anodal/cathodal waveforms to stimulate distal brain structures.

A further embodiment describes improving mitochondrial function in spinocerebellar ataxia by the application of biphasic anodal/cathodal waveforms to stimulate distal brain structures.

An embodiment describes improving mitochondrial function in Alzheimer's disease by the application of biphasic anodal/cathodal waveforms to stimulate distal brain structures.

Another embodiment describes stimulating hormone secreting cells by the application of biphasic anodal/cathodal waveforms.

An embodiment describes stimulating the release of insulin from the pancreas by the application of biphasic anodal/cathodal waveforms.

Embodiments of the present disclosure may also be as set forth in the following parentheticals.

(1) A method of healing skin wounds, comprising: guiding cell migration at the skin wound by applying biphasic waveforms including a positive anodal pulse followed by a negative cathodal pulse to the wound.

(2) A method for interrupting epileptic seizures, comprising: applying biphasic waveforms including a positive anodal pulse followed by a negative cathodal pulse to nerves to stimulate distal brain structures.

(3) The method of (2), further comprising applying the biphasic waveforms to the nerves via electrodes implanted in a brain.

(4) The method of (2), further comprising stimulating distal brain structures by applying the biphasic waveforms via electrodes implanted in a left-side vagus nerve of a patient.

(5) The method of (2), further comprising stimulating distal brain structures by applying the biphasic waveforms via electrodes attached to a scalp of a patient.

(6) The method of (2), further comprising applying, by a pulse generator, the positive anodal pulse for a pulse length of t milliseconds; and applying, by the pulse generator, the negative cathodal pulse for a pulse length of k milliseconds, wherein t is greater than k, t is equal to k, or t is less than k.

(7) The method of (2), further comprising applying, by a pulse generator, a square wave voltage of positive amplitude $V_1$ to an anodal electrode; and applying, by the pulse generator, a square wave voltage of negative amplitude $V_2$ to an cathodal electrode, wherein $V_1$ is less than or equal to $V_2$.

(8) The method of any one of (2) or (3), further comprising: sensing, by a sensing circuit connected to the electrodes, electrical signals in the brain which indicate an onset of an epileptic seizure; and applying the biphasic anodal and the cathodal pulses when the sensing circuit detects the onset of the epileptic seizure.

(9) A method for improving mitochondrial function in Alzheimer's disease, comprising: applying biphasic waveforms including a positive anodal pulse followed by a negative cathodal pulse to nerves to stimulate distal brain structures.

(10) The method of (9), further comprising: stimulating distal brain structures by applying, by a pulse generator, the biphasic waveforms via electrodes implanted in a left-side vagus nerve of a patient.

(11) The method of claim 9, further comprising: stimulating distal brain structures by applying, by a pulse generator, the biphasic waveforms via electrodes attached to a scalp of a patient.

(12) A method for stimulating hormone secreting cells, comprising: applying biphasic waveforms including a positive anodal pulse followed by a negative cathodal pulse via electrodes located in a conduction pathway of a hormone secreting organ.

(13) A method for stimulating the release of insulin from the pancreas, comprising: applying biphasic waveforms including a positive anodal pulse followed by a negative cathodal pulse via electrodes located in a conduction pathway of the pancreas.

(14) A method of lowering the membrane potential (MP) of a cell below the resting membrane potential (RMP), comprising: changing the cell membrane permeability by stimulating electrodes contacting an electric conduction pathway of the cell with a positive anodal pulse followed by a negative cathodal pulse.

(15) A method for improving mitochondrial function in glutan ataxia, comprising: applying biphasic waveforms including a positive anodal pulse followed by a negative cathodal pulse to nerves to stimulate distal brain structures.

(16) A method for improving mitochondrial function in spinocerebellar ataxia, comprising: applying biphasic waveforms including a positive anodal pulse followed by a negative cathodal pulse to nerves to stimulate distal brain structures.

(17) The method of (16), further comprising: stimulating distal brain structures by applying, by a pulse generator, the biphasic waveforms via electrodes implanted in on a tenth cranial nerve of a patient.

(18) The method of (16), further comprising: stimulating distal brain structures by applying, by a pulse generator, the biphasic waveforms via electrodes attached to a scalp of a patient.

(19) The method of (16), comprising: applying, by a pulse generator, a square wave voltage of positive amplitude $V_1$ to an anodal electrode; and applying, by the pulse generator, a square wave voltage of negative amplitude $V_2$ to an cathodal electrode, wherein $V_1$ is less than or equal to $V_2$.

(20) A system for stimulating nerves, comprising: a pulse generator configured to generate biphasic waveforms including a positive anodal pulse followed by a negative cathodal pulse; electrodes connected to the pulse generator by wires, wherein the electrode are configured to be connected to a nerve conduction pathway; and a programmable computing unit connected to the pulse generator, wherein the programmable computing unit includes circuitry and program instructions stored therein that, when executed by one or more processors, cause the one or more processors to signal the pulse generator to generate the biphasic waveforms.

Obviously, numerous modifications and variations of the present invention are possible in light of the above teachings. It is therefore to be understood that within the scope of the appended claims, the invention may be practiced otherwise than as specifically described herein.

The invention claimed is:

1. A method for interrupting epileptic seizures, comprising:
   placing a first electrode inside an axon of a nerve;
   placing a second electrode on a cytoplasmic surface of the axon; and
   applying biphasic waveforms to the nerve by way of the first and second electrodes, said biphasic waveforms including a positive anodal pulse followed immediately by an inverse negative symmetric cathodal pulse to the nerve to lower a membrane potential of the nerve below a resting membrane potential of the nerve and thereby facilitate stimulation of distal brain structures to effectuate interruption of an epileptic seizure.

2. The method of claim 1, further comprising: applying the biphasic waveforms to nerves via electrodes implanted in a brain.

3. The method of claim 2, further comprising:
sensing, by a sensing circuit connected to the first and second electrodes, electrical signals in the brain which indicate an onset of an epileptic seizure; and
applying the biphasic anodal and the cathodal pulses when the sensing circuit detects the onset of the epileptic seizure.

4. The method of claim 1, wherein the nerve is a left-side vagus nerve of a patient.

5. The method of claim 4, further comprising:
applying, by a pulse generator via the first electrode and second electrode, the positive anodal pulse for a pulse length of t milliseconds; and
applying, by the pulse generator via the first electrode and second electrode, the negative cathodal pulse for a pulse length of k milliseconds, wherein t is greater than k, t is equal to k, or l is less than k.

6. The method of claim 1, further comprising:
stimulating the distal brain structures by further applying the biphasic waveforms via electrodes attached to a scalp of a patient.

7. A method for improving mitochondrial function in Alzheimer's disease, comprising:
placing a first electrode inside an axon of a nerve;
placing a second electrode on a cytoplasmic surface of the axon; and
applying biphasic waveforms to the nerve by way of the first and second electrodes, said biphasic waveforms including a positive anodal pulse followed immediately by an inverse negative symmetric cathodal pulse to the nerve to lower a membrane potential of the nerve below a resting membrane potential of the nerve and thereby facilitate stimulation of distal brain structures to effectuate interruption of an epileptic seizure.

8. The method of claim 7, further comprising:
stimulating said distal brain structures by applying, by a pulse generator, the biphasic waveforms via the first and second electrodes, wherein the first and second electrodes are implanted in a left-side vagus nerve of a patient.

9. The method of claim 7, further comprising:
stimulating said distal brain structures by further applying, by a pulse generator, the biphasic waveforms via electrodes attached to a scalp of a patient.

* * * * *